United States Patent
Fujimoto et al.

(10) Patent No.: US 10,182,894 B2
(45) Date of Patent: Jan. 22, 2019

(54) METHOD FOR MANUFACTURING DENTAL PROSTHESIS

(71) Applicant: GC CORPORATION, Tokyo (JP)

(72) Inventors: Tatsuya Fujimoto, Tokyo (JP); Masatoshi Yoshinaga, Tokyo (JP); Go Mashio, Tokyo (JP); Daisuke Ohta, Tokyo (JP)

(73) Assignee: GC CORPORATION, Tokyo (JP)

( * ) Notice: Subject to any disclaimer, the term of this patent is extended or adjusted under 35 U.S.C. 154(b) by 135 days.

(21) Appl. No.: 15/119,552

(22) PCT Filed: Feb. 18, 2015

(86) PCT No.: PCT/JP2015/054385
§ 371 (c)(1),
(2) Date: Aug. 17, 2016

(87) PCT Pub. No.: WO2015/125807
PCT Pub. Date: Aug. 27, 2015

(65) Prior Publication Data
US 2017/0056139 A1    Mar. 2, 2017

(30) Foreign Application Priority Data
Feb. 21, 2014 (JP) .................. 2014-031851

(51) Int. Cl.
*A61C 13/08* (2006.01)
*B29C 41/04* (2006.01)
(Continued)

(52) U.S. Cl.
CPC ............ *A61C 13/081* (2013.01); *A61C 13/08* (2013.01); *A61C 13/09* (2013.01); *A61C 13/20* (2013.01);
(Continued)

(58) Field of Classification Search
CPC ....... A61C 13/081; A61C 13/09; A61C 13/08; A61C 13/20; B29C 41/22; B29C 41/04; B29L 2031/753; B29K 2101/12
See application file for complete search history.

(56) References Cited

U.S. PATENT DOCUMENTS

| 1,511,458 A | 10/1924 | Gibson |
| 6,648,646 B2 | 11/2003 | Sato |
(Continued)

FOREIGN PATENT DOCUMENTS

| CN | 1197528 C | 4/2005 |
| CN | 1960849 A | 5/2007 |
(Continued)

OTHER PUBLICATIONS

International Search Report dated Apr. 28, 2015; PCT/JP2015/054385.

*Primary Examiner* — Robert J Grun
(74) *Attorney, Agent, or Firm* — Ladas & Parry LLP; Loren K. Thompson (57) ABSTRACT

An object is to provide a method for manufacturing a dental prosthesis consisting of a plurality of layers with high productivity. The method for manufacturing a dental prosthesis comprises: filling a cavity (21a) formed in a mold which has a shape of the dental prosthesis with a layered material body (23) that is made by layering materials (23a, 23b) corresponding to the plurality of layers; and after this filling, rotating the mold on a material inlet (21b) of the mold and cutting the materials.

2 Claims, 9 Drawing Sheets

(51) Int. Cl.
 *B29C 41/22* (2006.01)
 *A61C 13/09* (2006.01)
 *A61C 13/20* (2006.01)
 *B29K 101/12* (2006.01)
 *B29L 31/00* (2006.01)

(52) U.S. Cl.
 CPC .............. *B29C 41/04* (2013.01); *B29C 41/22* (2013.01); *B29K 2101/12* (2013.01); *B29L 2031/753* (2013.01)

(56) References Cited

U.S. PATENT DOCUMENTS

2008/0023872 A1  1/2008  Criel
2009/0239199 A1  9/2009  Cadario et al.

FOREIGN PATENT DOCUMENTS

| CN | 1988995 A | 6/2007 |
|---|---|---|
| JP | 5734844 A | 2/1982 |
| JP | 06269466 A | 9/1994 |
| JP | 2010-503474 A | 2/2010 |
| WO | 2013066282 A1 | 5/2013 |

METHOD FOR MANUFACTURING DENTAL PROSTHESIS

TECHNICAL FIELD

This invention relates to a method for manufacturing a dental prosthesis, and more particularly relates to a method for manufacturing a dental prosthesis including a plurality of layers.

BACKGROUND ART

A dental prosthesis such as a crown is one means for artificially reproducing functions of a lost natural tooth. An exterior of a natural tooth is formed hard by enamel and has a unique texture. A natural tooth affects not only the function of mastication but also impression of a human's face. Thus, preferably, a dental prosthesis having as close color and texture to a natural tooth as possible is used. As one method for improving so-called aesthetics of a dental prosthesis as described, for example, Patent Literature 1 proposes a dental prosthesis that consists of a plurality of layers having an inside layer of low transparency and an outside layer of high transparency as disclosed. According to this, the inside layer shields the color of an abutment from the exterior view, and the aesthetic property can be improved by the outer layer of high transparency and the inside layer seen through the outer layer.

Patent Literature 1 discloses that the inner layer is cast first and then, the outer layer is cast on the inner layer as a method for manufacturing such a dental prosthesis having a plurality of layers.

CITATION LIST

Patent Literature

Patent Literature 1: JP H6-269466A

SUMMARY OF INVENTION

Technical Problem

There is a problem that it takes some effort to form a dental prosthesis consisting of a plurality of layers with the manufacturing method as described in Patent Literature 1, and it is demanded that the productivity be improved.

In view of the above problem, an object of this invention is to provide a method for manufacturing a dental prosthesis consisting of a plurality of layers with high productivity.

Solution to Problem

The present invention will be described below. Here, reference signs attached to the drawings are described together in parentheses for easy understanding. However, the present invention is not limited thereto.

The invention of claim 1 is a method for manufacturing a dental prosthesis (10) that has a plurality of layers (11, 12), the method comprising: filling a cavity (21a) that has a shape of the dental prosthesis with a layered material body (23) that is made by layering materials (23a, 23b) corresponding to the plurality of layers, the cavity being formed in a mold (21); and after said filling, rotating the mold on a material inlet (21b) of the mold and cutting the materials.

In the invention of claim 2, all of an outer circumference of the dental prosthesis is covered by one kind of the layers in the method for manufacturing a dental prosthesis according to claim 1.

Advantageous Effects of Invention

According to the present invention, the productivity can be improved because it is not necessary to individually make a plurality of layers of a dental prosthesis but the layers can be formed at the same time.

DESCRIPTION OF EMBODIMENTS

The above described operation and advantage of the present invention are made clear by the embodiments described as follows. The present invention will be described below based on the embodiments shown in the drawings. However, the present invention is not limited to these embodiments.

Figure 1:
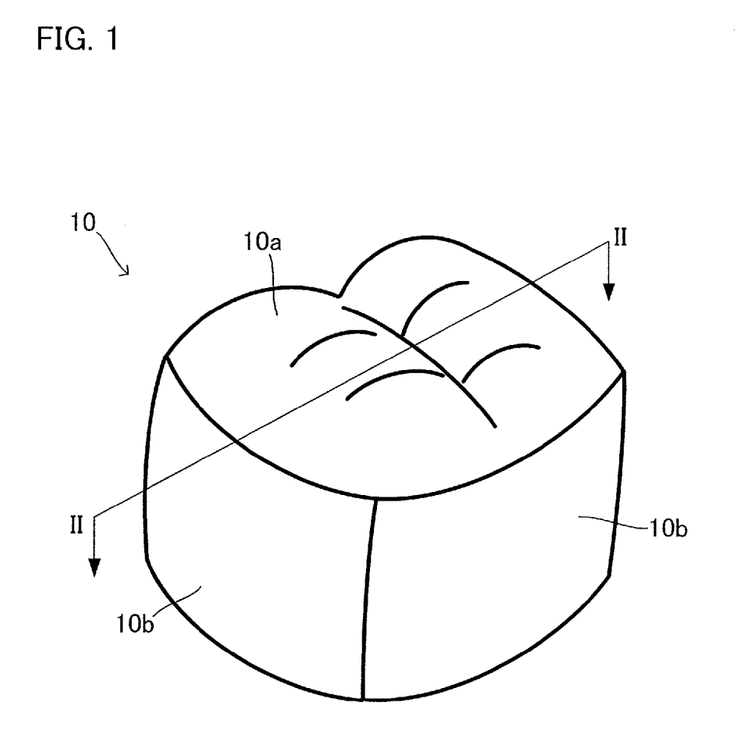
FIG. 1 is an exterior perspective view of a dental prosthesis 10.
Figure 2:
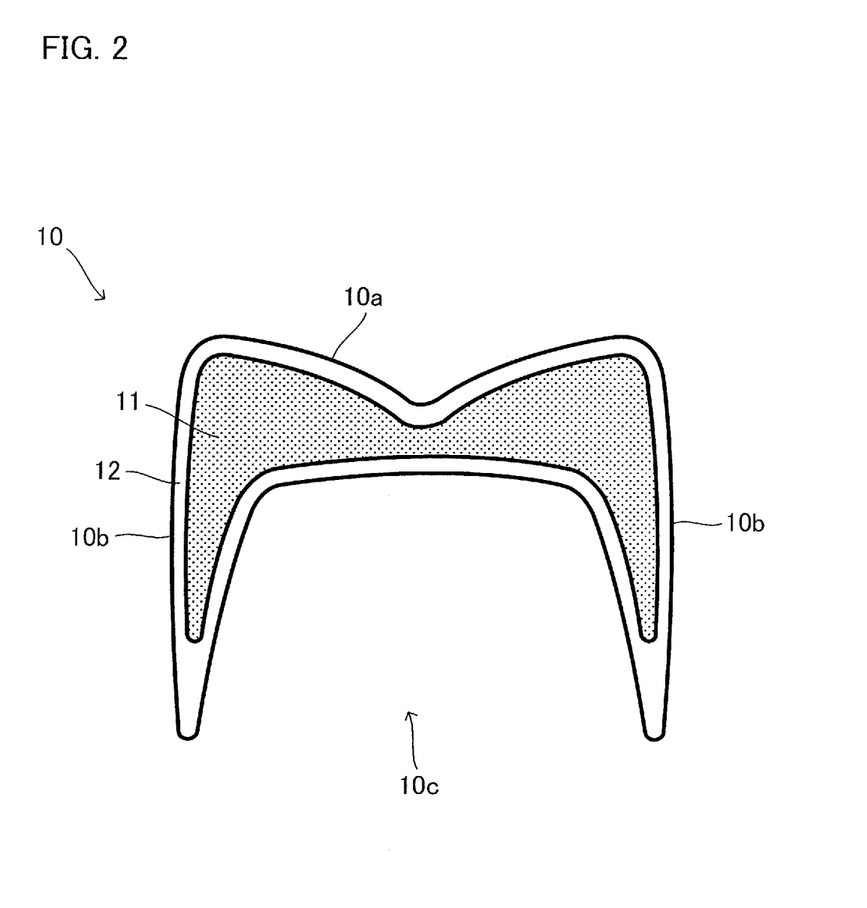
FIG. 2 is a cross-sectional view of the dental prosthesis 10.

Before describing a method for manufacturing a dental prosthesis, one example of a shape of a dental prosthesis manufactured by this method is described. FIG. 1 is an exterior perspective view of a dental prosthesis 10 that is the example. FIG. 2 is a cross-sectional view taken along the line II-II in FIG. 1 in the direction of the arrows. As is seen from FIGS. 1 and 2, the dental prosthesis 10 of this example is a crown. Intraoral side surface 10a and side surface 10b have shapes that imitate a natural tooth. In contrast, the side of the dental prosthesis 10 which faces the intraoral side surface 10a is an abutment side surface 10c that has a shape like a recess. An abutment is inserted to this portion, which is shaped to be like a recess, to retain the dental prosthesis 10 in an oral cavity.

The dental prosthesis 10 of this example is formed to have an inner layer 11 and an outer layer 12 as is seen from FIG. 2.

The inner layer 11 has color close to a natural tooth, and functions so that the dental prosthesis 10 resembles a natural tooth as a whole. The inner layer 11 is structured so as to hide an abutment from the outer view when the dental prosthesis 10 is attached to the abutment. Thereby, impression closer to a natural tooth can be given because the abutment cannot be seen.

In view of the above, the inner layer 11 has color close to a natural tooth, and is constituted by a material whose transparency is kept low. Examples of a material used for the inner layer 11 in view of this include thermoplastic resin, ceramics and glass ceramics. Ceramics and glass ceramics are preferable among them in view of the strength and aesthetics of the dental prosthesis.

The outer layer 12 is a layer that is formed so as to surround the outer circumference of the inner layer 11. In this example, the outer layer 12 is layered around all the circumference of the inner layer 11. The outer layer 12 has a function of making texture of the outer surface of the dental prosthesis 10 close to that of a natural tooth. Because of this, the outer layer 12 has color close to a natural tooth, and is constituted by a material whose transparency is higher than the inner layer 11.

Examples of a material used for the outer layer 12 in view of this include thermoplastic resin, ceramics and glass ceramics.

Ceramics and glass ceramics are preferable among them in view of the strength and aesthetics of the dental prosthesis.

Here, in view of easy molding and improvement of the aesthetics, preferably combination of materials of the inner layer 11 and the outer layer 12 is not combination of largely different materials in property such as thermoplastic resin and ceramics. It is more preferable to employ combination of different materials of similar properties.

Specific color of the inner layer 11 and the outer layer 12 is adjusted according to a patient's natural tooth and any other requirements. Such adjustment is carried out by a known method.

The dental prosthesis 10 of this example has the structure that all the circumference of the inner layer 11 is surrounded only by one kind of a layer (only by the outer layer 12) and thus the border between the inner layer 11 and the outer layer 12 is not exposed. Therefore, such faults can be held down that spots intrude between the inner layer 11 and the outer layer 12, which lowers the aesthetics.

Next, one embodiment will be described concerning the method for manufacturing a dental prosthesis that is formed by having a plurality of layers like the dental prosthesis 10. Here, an example of manufacturing the dental prosthesis 10 is described. However, the present invention is not necessarily limited thereto, and for example, a dental prosthesis of such an embodiment can be manufactured that the outer circumference is not formed by one kind of a layer only, and part of the inner layer 11 is exposed. FIGS. 3 to 9 are views for explanation. These drawings are conceptual drawings shown to explain this manufacturing method, and are not drawings showing modes and behaviors of materials precisely.

Figure 3:
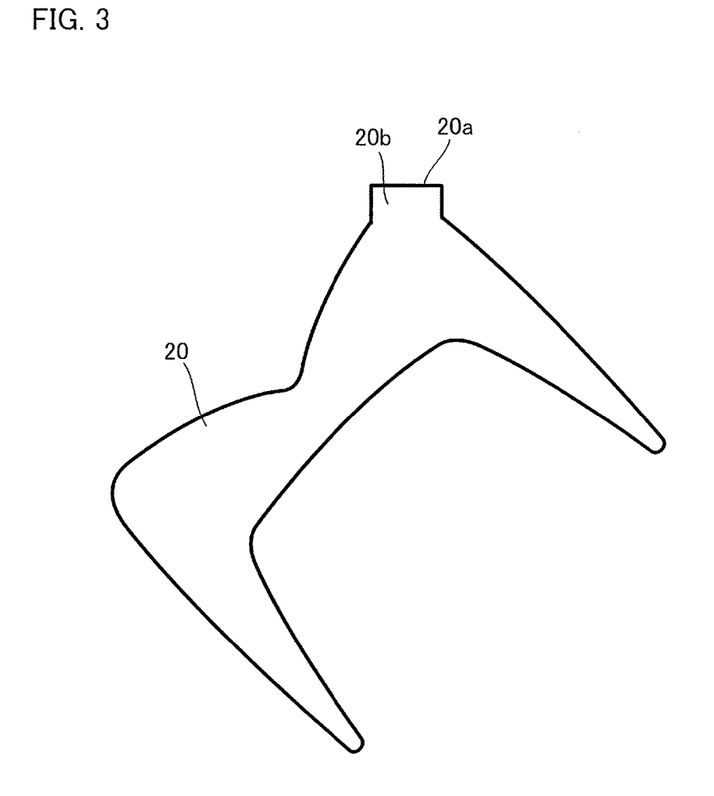
FIG. 3 shows a wax pattern 20.

In the manufacturing method of this embodiment, first, a wax pattern 20 of the dental prosthesis 10 that is to be manufactured is made as shown in FIG. 3 by a known method. In making, an end surface for an opening 20a and a passage forming part 20b which are for forming a passage where materials pass when a mold 21 (see FIG. 4) is made are provided together.

Figure 4:
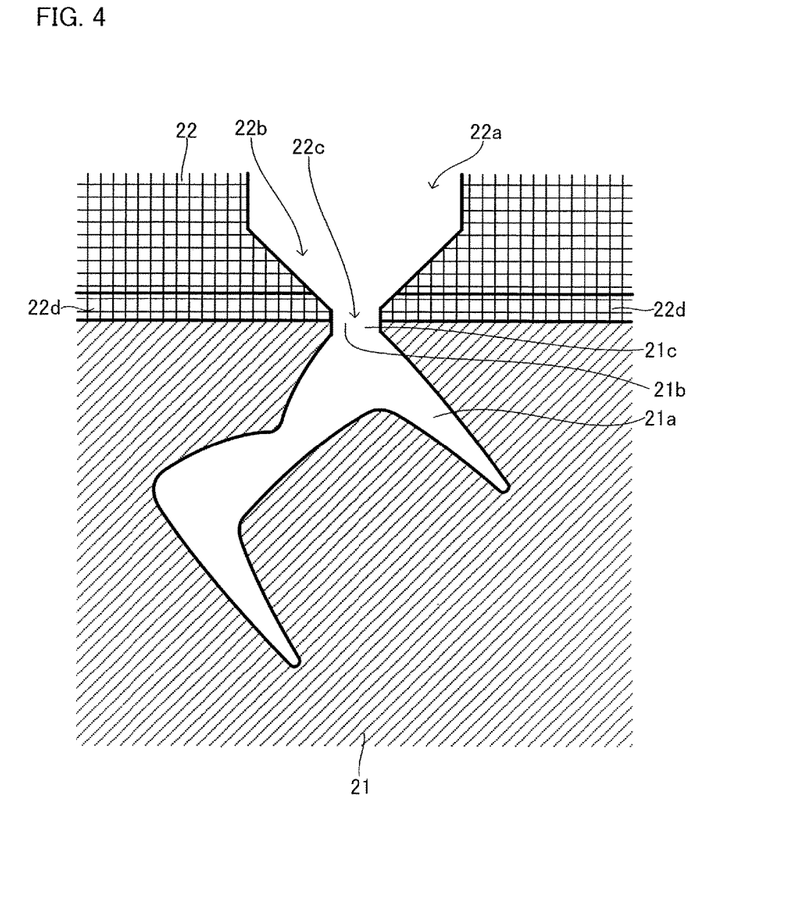
FIG. 4 is a view to explain the scene where a mold 21 is attached to a filling device 22.

Next, the wax pattern 20 is invested in dental investment. After the dental investment is cured, the wax pattern 20 is liquated out and combusted, to be removed. Thereby, the mold 21 shown in FIG. 4 is made. Thus, in the mold 21, a cavity 21a having a shape of the dental prosthesis 10, material inlet 21b where materials are forced, and a passage 21c that is a passage linking the material inlet 21b with the cavity 21a are formed.

The mold 21 formed like the above is attached to a filling device 22 as shown in FIG. 4. The filling device 22 includes a material insertion part 22a that is a space for disposing a block-like layered material body 23 (see FIG. 5), a reduced diameter part 22b that is a space whose diameter is continuously reduced from the material insertion part 22a, a material inlet 22c for filling the mold 21 with materials at an end part of the reduced diameter part 22b, and a pressing member that presses the layered material body 23 toward the material inlet 22e side, which is not depicted. Here, the filling device 22 is provided with a shutter 22d that closes the material inlet 22c and cuts materials. The filling device 22 is further structured so that, assuming that a direction parallel to the pressing direction is an axis, the mold 21 can be rotated on the axis.

When the mold 21 is attached to the filling device 22, as shown in FIG. 4, they are arranged so that the material inlet 22c of the filling device 22 communicates with the material inlet 21b of the mold 21.

Figure 5:
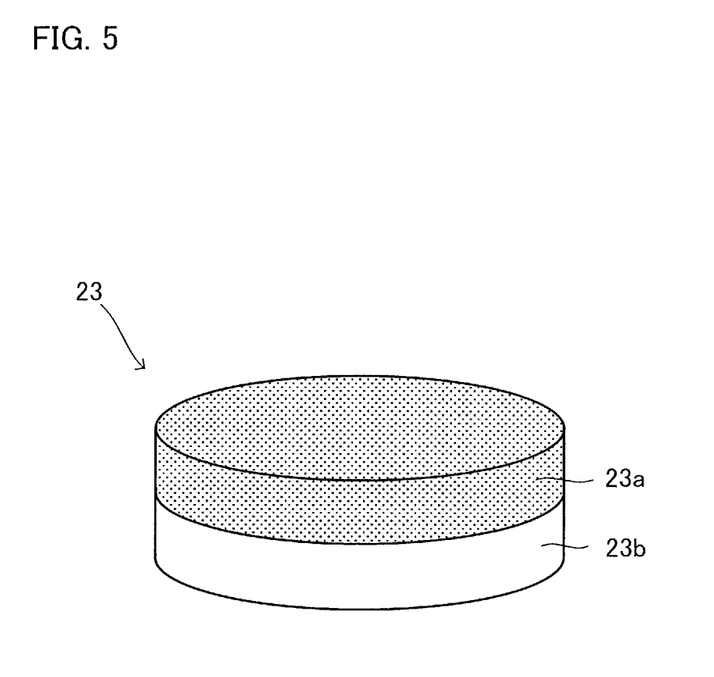
FIG. 5 is an exterior perspective view of a layered material body 23.

FIG. 5 is a perspective view of the block-like layered material body 23, which is used as materials that form the dental prosthesis 10. In this embodiment, the layered material body 23 is a columnar shape correspondingly to the shape of the material insertion part 22a of the filling device 22. A material for an inner layer 23a and a material for an outer layer 23b are layered in a direction along the axis of the columnar shape. The materials each are to constitute the inner layer 11 and the outer layer 12, and are as described above.

Figure 6:
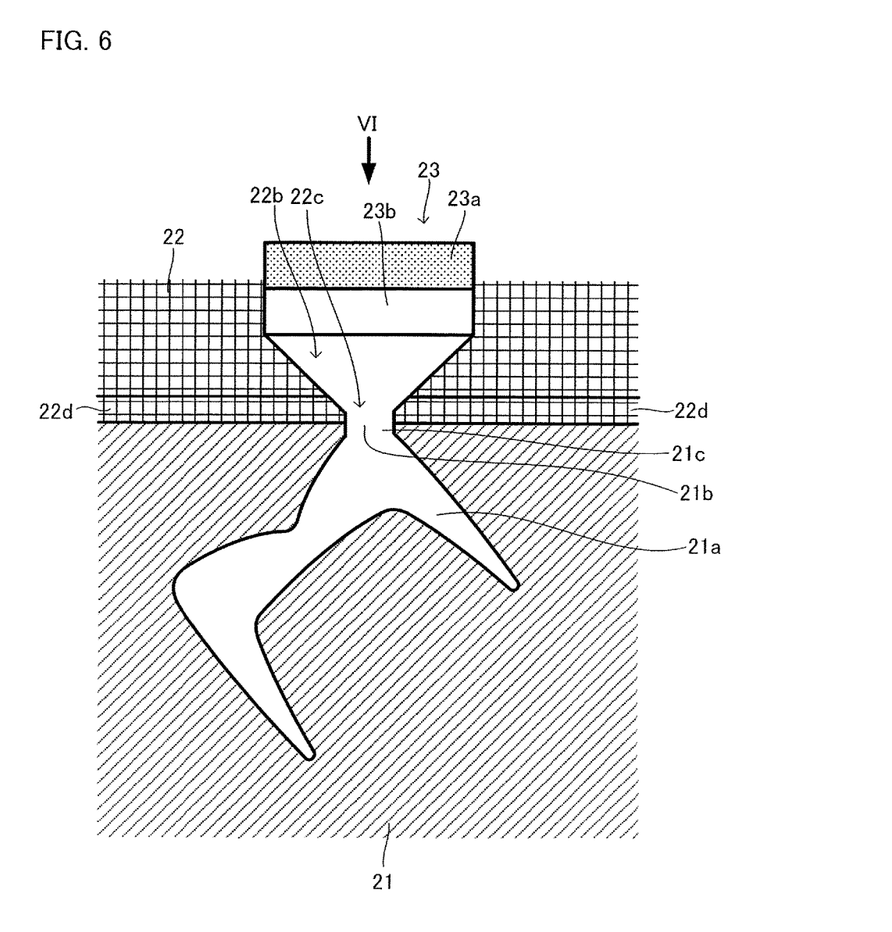
FIG. 6 is a view to explain one scene of molding the dental prosthesis 10.

Next, as shown in FIG. 6, the layered material body 23 is arranged in the material insertion part 22a of the filling device 22. At this time, the material for an outer layer 23b faces the mold 21 side and the material for an inner layer 23a faces the opposite side to the mold 21 (a side of the pressing member not shown). The layered material body 23 is heated to a predetermined temperature that is lower than melting temperature in order to decrease the viscosity.

The layered material body 23 is pressed by the pressing member not shown from the state shown in FIG. 6 in the direction indicated by VI in FIG. 6. Thereby, the layered material body 23, whose viscosity is decreased, passes through the reduced diameter part 22b and the material inlet 22c, enters the mold 21 through the material inlet 21b, and passes through the passage 21c, and the cavity 21a is filled therewith as shown in FIG. 7.

Figure 7:
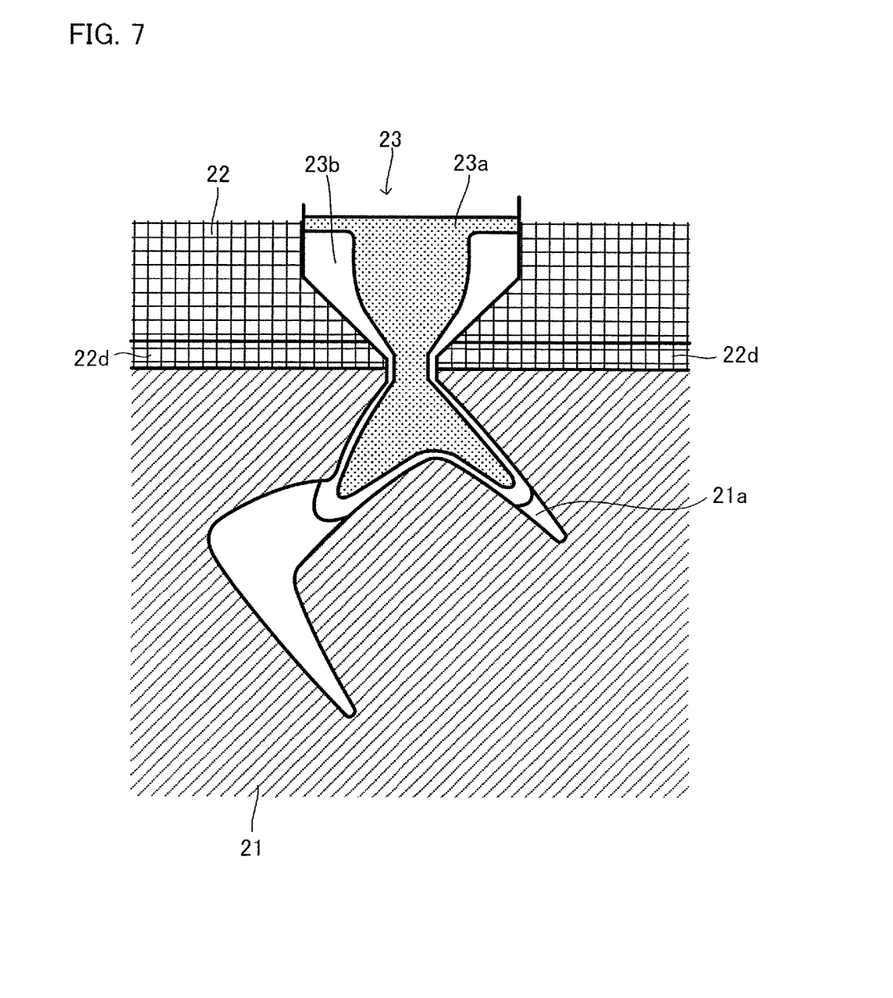
FIG. 7 is a view to explain a process of filling with materials.

At this time, as shown in FIG. 7, the cavity 21a is filled with the layered material body 23, whose viscosity is decreased, as the material for an inner layer 23a, which is in the side further from the mold 21, moves forward inside the material for an outer layer 23b, which is in the side closer to the mold 21, the material for an outer layer 23b covers the inner circumferential face of the cavity 21a, and the material for an inner layer 23a moves forward inside the covered inner circumferential face. Thereby, as shown in FIG. 8, when filling (pressing) is completed, the shape and the layer structure of the dental prosthesis 10 to be obtained are simultaneously formed.

Figure 8:
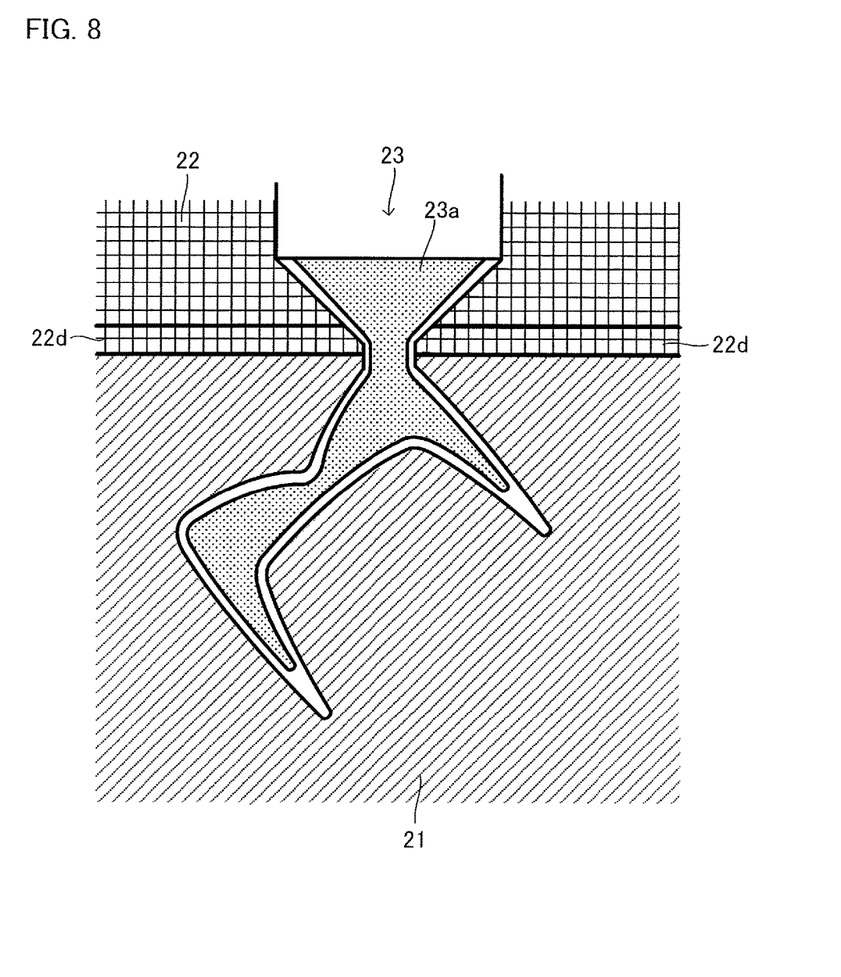
FIG. 8 is a view to explain the scene where filling with the materials is completed.
Figure 9:
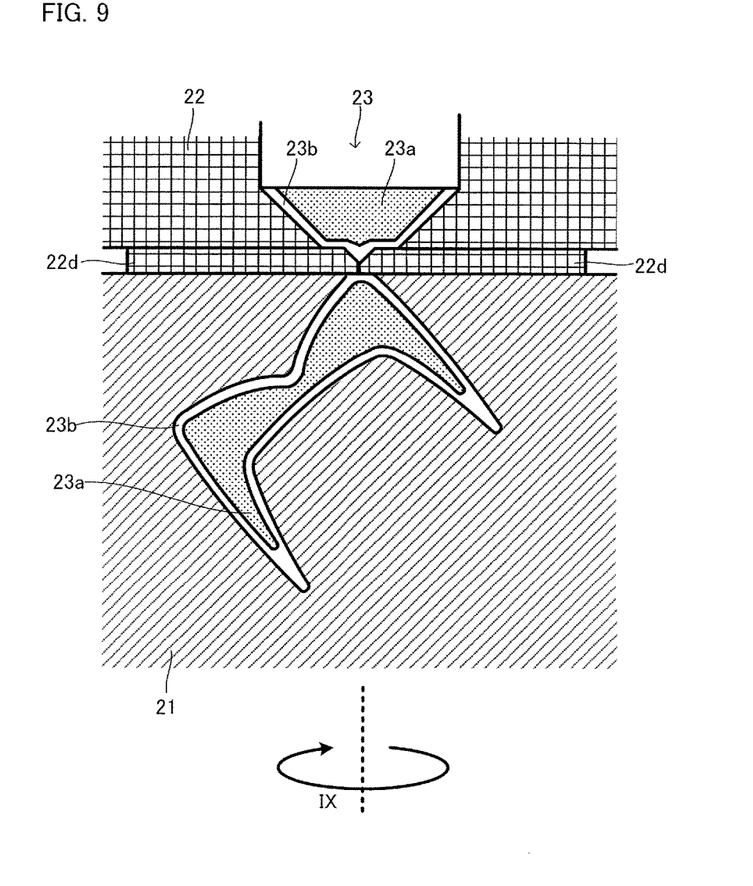
FIG. 9 is a view to explain the scene of rotating the mold 21 and cutting the materials.

Under the state shown in FIG. 8, the materials communicate between the mold 21 side and the filling device 22 side. Thus, it is necessary to isolate the mold 21 from the filling device 22. Just pulling or sliding might bring the situation where the material for an inner layer 23a is exposed outside at this portion. In contrast, in the manufacturing method of this embodiment, as shown in FIG. 9, the mold 21 is rotated on the pressing axis (the axis of the pressing) as the center as indicated by IX in FIG. 9, and further, the shutter 22d provided for the filling device 22 is closed; whereby the material inlet 22c is closed, the materials are cut, and the mold 21 is isolated from the filling device 22. Thereby, the material for an outer layer 23b covers the material for an inner layer 23*a* even at the portion of the material inlet 21*b* of the mold 21, and the material for an inner layer 23*a* can be prevented from being exposed.

At this time, the number of rotations of the mold 21 is preferably 1 rpm to 100 rpm. More preferably, 10 rpm to 70 rpm. Less than 1 rpm of the number of rotations results in bad productivity More than 100 rpm of the number of rotations might make the above described effect deteriorate.

The materials with which the mold 21 is filled are cooled down and separated from the mold, and then the dental prosthesis 10 may be taken out.

According to the manufacturing method as described above, a plurality of layers can be formed just once simultaneously, and a dental prosthesis can be manufactured efficiently. When the mold is removed from the filling device, the mold 21 is rotated and the shutter 22*d* is used as described above; thereby the material for an inner layer 23*a* can be properly arranged inside the material for an outer layer 23*b* even at the portion of the material inlet.

In this embodiment, an example of making the mold 21 using the wax pattern 20 is described in view of matching an individual patient. This invention is not limited to this example, and when a dental prosthesis of an embodiment for multiple uses which has an average shape is manufactured, the above method may be carried out with using a die as a mold with which the dental prosthesis of an embodiment for multiple uses can be obtained.

REFERENCE SIGNS LIST

10 dental prosthesis
11 inner layer
12 outer layer
20 wax pattern
21 mold
21*a* cavity
21*b* material inlet
21*c* passage
22 filling device
22*a* material insertion part
22*b* reduced diameter part
22*c* material inlet
22*d* shutter
23 layered material body
23*a* material for an inner layer
23*b* material for an outer layer

The invention claimed is:

1. A method for manufacturing a dental prosthesis that has a plurality of layers, the method comprising:
   filling a cavity that has a shape of the dental prosthesis with a layered material body that is made by layering at least two kinds of materials corresponding to the plurality of layers, the cavity being formed in a mold, by injecting/casting the materials into the mold at the same time; and
   after said filling, rotating the mold on a material inlet of the mold and cutting the materials.

2. The method for manufacturing a dental prosthesis according to claim 1, wherein all of an outer circumference of the dental prosthesis is covered by one kind of the layers.

* * * * *